(12) United States Patent
Heidenreich et al.

(10) Patent No.: US 8,410,014 B2
(45) Date of Patent: Apr. 2, 2013

(54) METHOD FOR PRODUCING CATALYSTS AND THEIR USE FOR THE GAS PHASE OXIDATION OF OLEFINS

(75) Inventors: Roland Heidenreich, Munich (DE); Hans-Jurgen Eberle, Munich (DE); Johann Weis, Sauerlach (DE)

(73) Assignee: Wacker Chemie AG, Munich (DE)

( * ) Notice: Subject to any disclaimer, the term of this patent is extended or adjusted under 35 U.S.C. 154(b) by 722 days.

(21) Appl. No.: 12/518,520

(22) PCT Filed: Dec. 6, 2007

(86) PCT No.: PCT/EP2007/063380
§ 371 (c)(1),
(2), (4) Date: Jun. 10, 2009

(87) PCT Pub. No.: WO2008/071610
PCT Pub. Date: Jun. 19, 2008

(65) Prior Publication Data
US 2010/0022796 A1    Jan. 28, 2010

(30) Foreign Application Priority Data
Dec. 13, 2006  (DE) .................. 10 2006 058 800

(51) Int. Cl.
*B01J 23/00* (2006.01)
*B01J 21/00* (2006.01)
*B01J 29/00* (2006.01)
*B01J 37/00* (2006.01)
*B01J 20/00* (2006.01)
*B01J 35/00* (2006.01)
*C07C 67/00* (2006.01)

(52) U.S. Cl. ........ 502/237; 502/240; 502/243; 502/250; 502/253; 502/258; 502/261; 502/262; 502/263; 502/300; 502/304; 502/326; 502/327; 502/328; 502/330; 502/332; 502/333; 502/334; 502/339; 502/340; 502/341; 502/344; 502/349; 502/350; 502/351; 502/355; 502/415; 502/439; 560/208

(58) Field of Classification Search ............. 502/237, 502/240, 243, 250, 253, 258, 261, 262, 263, 502/300, 304, 326, 327, 328, 330, 332, 333, 502/334, 339, 340, 341, 344, 349, 350, 351, 502/355, 415, 439; 264/5
See application file for complete search history.

(56) References Cited

U.S. PATENT DOCUMENTS

| | | | |
|---|---|---|---|
| 3,923,692 A * | 12/1975 | Braithwaite et al. ........... 502/238 |
| 4,048,096 A | 9/1977 | Bissot | |
| 4,052,334 A * | 10/1977 | Mockett ........................ 502/439 |
| 4,093,559 A | 6/1978 | Fernholz et al. | |
| 4,113,658 A * | 9/1978 | Geus ............................. 502/242 |
| 4,272,409 A * | 6/1981 | Bergna ............................. 502/8 |
| 4,482,642 A | 11/1984 | Ettlinger et al. | |
| 4,602,000 A * | 7/1986 | Dupin et al. ................... 502/335 |
| 4,680,043 A | 7/1987 | Ginter et al. | |
| 4,698,324 A * | 10/1987 | Haruta et al. .................. 502/243 |
| 4,937,219 A * | 6/1990 | Haruta et al. .................. 502/174 |
| 5,002,918 A | 3/1991 | Deller et al. | |
| 5,021,378 A | 6/1991 | Deller et al. | |
| 5,030,433 A | 7/1991 | Mehrotra | |
| 5,128,114 A * | 7/1992 | Schwartz ....................... 423/335 |
| 5,175,136 A * | 12/1992 | Felthouse ....................... 502/242 |
| 5,189,123 A * | 2/1993 | Gropper et al. ................ 526/106 |
| 5,352,645 A * | 10/1994 | Schwartz ....................... 502/262 |
| 5,389,582 A * | 2/1995 | Loxley et al. ...................... 501/4 |
| 5,422,329 A * | 6/1995 | Wirtz et al. .................... 502/328 |
| 5,476,963 A | 12/1995 | Wirtz et al. | |
| 5,723,402 A * | 3/1998 | Pullukat et al. ................ 502/232 |
| 6,012,304 A * | 1/2000 | Loxley et al. ..................... 65/111 |
| 6,048,490 A * | 4/2000 | Cornelius et al. ............. 264/631 |
| 6,113,829 A * | 9/2000 | Bookbinder et al. ..... 264/211.11 |
| 6,200,517 B1 * | 3/2001 | Peng et al. ..................... 264/630 |
| 6,207,610 B1 | 3/2001 | Krause et al. | |
| 6,228,800 B1 * | 5/2001 | Yamaguchi et al. .......... 502/339 |
| 6,287,510 B1 * | 9/2001 | Xun .............................. 264/630 |
| 6,313,061 B1 * | 11/2001 | Denton et al. ................ 502/236 |
| 6,329,315 B1 * | 12/2001 | Denton et al. ................ 502/232 |
| 6,355,587 B1 * | 3/2002 | Loxley et al. .................... 501/54 |
| 6,383,273 B1 * | 5/2002 | Kepner et al. ............... 106/15.05 |
| 6,420,308 B1 * | 7/2002 | Khanmamedova ........... 502/344 |
| 6,491,861 B1 * | 12/2002 | Grosch et al. ................. 264/628 |
| 6,506,336 B1 * | 1/2003 | Beall et al. .................... 264/630 |
| 6,734,131 B2 * | 5/2004 | Shih et al. ..................... 502/340 |
| 6,783,724 B2 * | 8/2004 | Noguchi et al. .............. 264/631 |
| 6,818,254 B1 * | 11/2004 | Hoke et al. ................. 427/421.1 |
| 6,821,922 B1 | 11/2004 | Tacke et al. | |
| 6,825,366 B2 * | 11/2004 | Cunningham et al. ........ 549/533 |

(Continued)

FOREIGN PATENT DOCUMENTS

| | | |
|---|---|---|
| DE | 4142898 A1 | 6/1993 |
| DE | 4142902 A1 | 6/1993 |
| DE | 19843693 A1 | 3/2000 |
| EP | 0072390 A2 | 2/1983 |
| EP | 0327722 A2 | 8/1989 |
| EP | 0327815 A1 | 8/1989 |
| EP | 0464633 A1 | 1/1992 |
| EP | 0565952 A1 | 10/1993 |
| EP | 0807615 A1 | 11/1997 |
| EP | 0997192 B1 | 10/2001 |
| JP | 2003-225570 A2 | 8/2003 |
| JP | 2008-530255 T2 | 8/2008 |

OTHER PUBLICATIONS

Detlev Koth and Horst Ferch, Chem.-Ing.-Tech. 52 (1980) Nr. 8, S. 628-634.

*Primary Examiner* — Cam N. Nguyen

(74) *Attorney, Agent, or Firm* — Brooks Kushman P.C.

(57) ABSTRACT

Especially physically stable metal oxide catalyst supports are prepared by suspending a metal oxide in a continuous phase, activating by fine dispersion, coagulation to a viscoelastic mass, shaping, drying, and calcining. The catalyst support thus prepared may be treated with catalytic agents to produce supported catalysts for olefin oxidation.

37 Claims, No Drawings

U.S. PATENT DOCUMENTS

| | | |
|---|---|---|
| 6,849,570 B2 * | 2/2005 | Hasenzahl et al. ............ 502/242 |
| 6,881,701 B2 * | 4/2005 | Jacobs .......................... 502/300 |
| 6,887,822 B2 * | 5/2005 | Hu ................................ 502/232 |
| 6,942,713 B2 * | 9/2005 | Ogunwumi et al. ............ 55/523 |
| 7,026,266 B2 * | 4/2006 | Chaudhari et al. ............ 502/155 |
| 7,030,056 B2 * | 4/2006 | Birke et al. ................... 502/330 |
| 7,256,153 B2 * | 8/2007 | Frenzel et al. ................. 502/243 |
| 7,425,647 B2 * | 9/2008 | Lemanski et al. ......... 560/241.1 |
| 7,507,687 B2 * | 3/2009 | Kodas et al. ................... 502/101 |
| 7,572,423 B2 * | 8/2009 | Kutsovsky .................... 423/337 |
| 7,601,671 B2 * | 10/2009 | LaBarge ....................... 502/326 |
| 7,659,224 B2 * | 2/2010 | Shimazaki et al. ............ 502/180 |
| 7,727,931 B2 * | 6/2010 | Brey et al. ..................... 502/344 |
| 7,759,009 B2 * | 7/2010 | Hennige et al. ............... 429/247 |
| 8,058,202 B2 * | 11/2011 | Brady et al. ................... 502/184 |
| 2003/0119648 A1 | 6/2003 | Werdecker et al. |
| 2003/0195114 A1 | 10/2003 | Tacke et al. |
| 2004/0072683 A1 * | 4/2004 | Kodas et al. ................... 502/224 |
| 2006/0070915 A1 | 4/2006 | Euzen et al. |
| 2008/0113162 A1 | 5/2008 | Barthel et al. |

* cited by examiner

METHOD FOR PRODUCING CATALYSTS AND THEIR USE FOR THE GAS PHASE OXIDATION OF OLEFINS

CROSS-REFERENCE TO RELATED APPLICATION

This application is the U.S. national phase of PCT Appln. No. PCT/EP2007/063380 filed Dec. 6, 2007 which claims priority to German application DE 10 2006 058 800.2 filed Dec. 13, 2006.

BACKGROUND OF THE INVENTION

1. Field of the Invention

The invention relates to a process for producing catalysts on stable, high-purity shaped bodies comprising pyrogenic metal oxides without additional binders and their use in the gas-phase oxidation of olefins.

2. Description of the Related Art

Pyrogenic metal oxides have an extremely small particle size, high specific surface areas, defined, spherical primary particles having a defined surface chemistry and do not have any internal surface (pores). Furthermore, they have a very high chemical purity.

Due to the properties outlined above, pyrogenic silicon dioxides, for example, are attracting increasing interest as, supports for catalysts (D. Koth, H. Ferch, Chem. Ing. Techn. 52, 628 (1980)).

However, owing to the particularly small particle size of pyrogenic metal oxides, the production of shaped bodies as are used, for example, as catalyst or catalyst support from these pyrogenic metal oxides is difficult. Shaped bodies comprising metal oxide powders are generally produced by pressing or extrusion using binders and lubricants in order to obtain stable shaped bodies. The binders and lubricants are inorganic and organic additives.

Inorganic additives, e.g. magnesium stearate, remain in the shaped bodies produced in the form of inorganic compounds, e.g. magnesium oxide. Organic additives, too, can result in impurities such as carbon in the production process for the shaped bodies. The desired very high purity of the pyrogenic metal oxides used, e.g. pyrogenic $SiO_2$, is therefore lost in the shaped bodies produced.

Apart from the high purity and the high surface area, a very low bulk density of the catalysts is a further desired property. This can, firstly, have a favourable effect on material transport in the future catalyzed reaction and, secondly, a low mass of support material is required in order to fill a particular reactor volume. This improves the cost ratio of support material to reactor volume and makes the process more economical.

Low bulk densities can be achieved, for example, by means of catalyst shapes which have at least one passage through them, for example rings.

Ring-shaped bodies having a very low wall thickness are particularly useful. However, low wall thicknesses lead to shaped bodies whose mechanical strengths are no longer sufficient for catalyst preparation and/or filling of the reactor and which are therefore unsuitable as catalyst support materials.

As catalytically active components, it is possible to use, inter alia, palladium and/or its compounds and alkali metal compounds, and additionally gold and/or its compounds (Pd/ alkali metal/Au system) or cadmium and/or its compounds (Pd/alkali metal/Cd system) or barium and/or its compounds (Pd/alkali metal/Ba system) or palladium, alkali metal compounds and mixtures of gold and/or cadmium and/or barium.

The prior art describes many possible ways of producing catalysts on shaped bodies comprising metal oxides. In these, binders or other strengthening steps are necessary to achieve later strength and the surface areas of the catalyst supports obtained require high bulk densities of the catalysts.

EP 72390 describes the production of pressed bodies from a mixture of pyrogenic metal oxides, water, silica sol and a pressing aid. A polyfunctional alcohol (e.g. glycerol) is claimed as an auxiliary.

EP 327722 discloses mixing pyrogenic silicon dioxide together with kaolin and/or graphite, sugar, starch, urea, wax into water. The pressed bodies can be produced using punch presses, excentric presses, extruders, rotary presses or compactors. An analogous procedure is employed in EP 327815, but a pyrogenic mixed oxide of silicon dioxide/aluminium oxide is used in place of pyrogenic silicon dioxide.

EP 807615 describes a process for producing pressed bodies comprising pyrogenic silicon dioxide, methylcellulose, microwax and polyethylene glycol and water. The pressed bodies usually comprise from 50 to 90% by weight of silicon dioxide, from 0.1 to 20% by weight of methylcellulose and from 0.1 to 15% by weight of microwax. and from 0.1 to 15% by weight of polyethylene glycol.

According to DE4142898, it is possible to produce stable shaped bodies from pyrogenic silica and aqueous-alcoholic ammonia solution. In contrast, a purely aqueous ammonia solution does not give a successful result. The high proportion of aqueous-alcoholic ammonia solution makes the mixture to be shaped strongly alkaline. The use of alcohol brings with it the risk of carbon contamination in the resulting catalyst support. According to DE4142902, stable shaped bodies can be obtained from pyrogenic silica and ammonia solution or from pyrogenic silica and silica sol containing alkali metal only when the shaped bodies are subjected to a hydrothermal treatment. In the case of the additional ammonia, the mixture once again becomes very alkaline. It is known that this excess of base (pH >10) leads to partial dissolution of $SiO_2$.

U.S. Pat. No. 4,048,096 describes the production of surface-impregnated Pd/Au catalysts in which the noble metals occur in a layer thickness of less than or equal to 0.5 mm from the outer surface of the support bodies. Alkali metal silicates are used as base for converting the soluble noble metal compounds into the respective noble metal hydroxides and a pH of 6.5-9.5 is set during this step for a time of 12-24 hours. Supports having surface areas of 10-800 square meters per gram are used as support materials for the VAM catalysts based thereon.

EP 807615 describes a process for producing pressed bodies comprising pyrogenic silicon dioxide, in which silicon dioxide is homogenized with methylcellulose, microwax and polyethylene glycol and an addition of water. After mixing, drying is carried out at from 80 to 150° C. The powder, which may-have been comminuted beforehand, is shaped to produce pressed bodies which are heat treated at temperatures of from 400 to 1200° C. for a period of from 0.5 to 8 hours. The mixtures before pressing the masses usually comprise from 50 to 90% by weight of silicon dioxide, from 0.1 to 20% by weight of methylcellulose and from 0.1 to 15% by weight of microwax and from 0.1 to 15% by weight of polyethylene glycol. The pressed bodies described in the examples have BET surface areas of from 120 to 210 $m^2$/g at pore volumes of from 0.71 to 0.97 ml/g. The pressed bodies having an external diameter of from 0.8 to 20 mm and a BET surface area of from 30 to 400 $m^2$/g claimed in the patent have a pore volume of from 0.5 to 1.3 ml/g. The shaped bodies having a bulk density of from 350 to 750 g/l comprise at least 99.8% by weight of silicon dioxide (other constituents <0.2% by weight) and achieve mechanical strengths of from 10 to 250 newton at an attrition of <5% by weight. Catalysts for preparing vinyl acetate monomer which are based on these support materials and contain palladium, gold and alkali metal acetate are claimed.

EP 997192 B1 describes supported palladium catalysts (Pd/Au/alkali metal, Pd/Cd/alkali metal or Pd/Ba/alkali metal systems) which are based on shaped bodies comprising pyrogenic mixed oxides. The shaped bodies on which the catalyst is based have an external diameter of from 0.8 to 25 mm, a BET surface area of from 5 to 400 m$^2$/g and a pore volume of from 0.2 to 1.8 ml/g and are composed of at least two oxides from the group consisting of $SiO_2$, $Al_2O_3$, $TiO_2$ and $ZrO_2$ in any order, but with the exception of $SiO_2/Al_2O_3$ mixed oxides, with other constituents being <1% by weight. In addition, the support materials described have compressive strengths of from 5 to 350 newton and bulk densities of from 250 to 1500 g/l. Catalysts which are based on these support materials and contain palladium, gold and alkali metal compounds or palladium, cadmium and alkali metal compounds or palladium, barium and alkali metal compounds are claimed. The alkali metal compound is potassium acetate in a preferred embodiment. The catalyst is used for preparing unsaturated esters, e.g. vinyl acetate monomer, in the gas phase.

EP 464633 describes a catalyst which has at least one passage having an internal diameter of at least one millimeter going through it and contains palladium and/or compounds thereof in an amount of from 1 to 20 gram/liter and, if appropriate, gold and/or compounds thereof in an amount of from 0.1 to 10 gram/liter. At least 95% of the palladium, gold and/or compounds thereof are present in a region from the surface to up to 0.5 mm below the surface of the support (surface-impregnated or coated catalyst). The catalyst is used for preparing unsaturated esters (e.g. vinyl acetate) by reaction of an olefin (e.g. ethene) with an organic carboxylic acid (e.g. acetic acid) and oxygen in the gas phase. In the examples, hydrazine hydrate is used as reducing agent.

The documents of the prior art show that the production of stable shaped bodies has hitherto not been possible without inorganic or organic additives such as extrusion aids, pore formers, sols or additional strengthening steps. Furthermore, the catalysts from the prior art display unfavourable bulk densities and low activities.

SUMMARY OF THE INVENTION

It is an object of the invention to improve on the prior art and provide catalysts which have lower bulk densities and are based on pyrogenic metal oxides, e.g. pyrogenic SiO2, and have very little contamination by metals, carbon and phosphorus, at the same time possess a high strength and have an improved selectivity and an increased activity compared to known catalysts. These and other objects are achieved by suspending a pyrogenic metal oxide in a solvent, converting the metal oxide into an active state by finely dispersing the metal oxide, coagulating the suspension into a paste-like mass, forming the paste-like mass into a shaped body, followed by drying and calcination, and applying a catalyst or precursor thereof to the shaped body.

DETAILED DESCRIPTION OF THE PREFERRED EMBODIMENTS

The invention thus provides a process for producing catalysts for the gas-phase oxidation of olefins, which comprises the steps:

(I) suspension of at least one pyrogenic metal oxide in a solvent,
(II) conversion of the metal oxide into an active state by producing a fine suspension by means of a dispersing apparatus and/or wet milling,
(III) coagulation of the suspension to give a paste-like mass,
(IV) conversion of the coagulated suspension into a shaped body,
(V) drying of the shaped body,
(VI) calcination of the shaped body obtained,
(VII) conversion of the shaped body into an active catalyst by application of one or more catalytically active compounds or one or more precursor compounds and/or one or more promoter compounds which can be converted in a subsequent step into one or more catalytically active compounds.

The pyrogenic metal oxide powders are obtained from flame hydrolysis or flame oxidation of a metal oxide precursor in a hydrogen/oxygen flame. Approximately spherical primary particles are initially formed and these sinter together during the reaction to form aggregates. The aggregates can subsequently clump together to form agglomerates. In contrast to the agglomerates which can generally be separated relatively easily into the aggregates by introduction of energy, the aggregates can be broken up further only by intensive introduction of energy, if at all.

As pyrogenic metal oxides, it is possible to use silicon oxide ($Si_xO_y$), aluminium oxide ($Al_xO_y$), titanium oxide ($Ti_xO_y$), zirconium oxide ($Zr_xO_y$), cerium oxide ($Ce_xO_y$) or mixtures of these metal oxides. Preference is given to using silicon oxide, most preferably silicon dioxide ($SiO_2$) (WACKER HDK® T40).

To produce the suspension, pyrogenic metal oxide powder or mixtures of various metal oxide powders are slowly introduced into a solvent, preferably water, by means of stirring energy. To avoid premature gelling, this preferably occurs within from 5 to 90 minutes.

To activate the metal oxides used, these are converted into a high-energy state by milling or by means of a dispersing apparatus. This is preferably carried out in the presence of a solvent, preferably water, which removes the heat evolved during processing. It is also possible to use organic solvents, but these incur the risk of carbon contamination of the future catalyst support. Particular preference is given to using water in high-purity form (Fe<2 ppb), as can be obtained, for example, by methods known from the literature or can be obtained commercially. Preference is given to using specially purified water which has a resistance of ≦18 MegaOhm*cm.

To produce the active, finely divided suspension, it has been found to be advantageous to mill the components in a frictional mill, for example an annular gap mill. In an annular gap mill, a centrally mounted milling cone rotates in a bell-shaped hollow cone. The material to be milled enters the mill at the bottom, is comminuted in the annular gap between the milling cone and the interior wall of the housing and leaves the mill in the upper part of the mill, which is also referred to as a bell mill. The suspension obtained can be collected in a container and recirculated to the inlet of the mill.

As an alternative to annular gap mills, it is also possible to use all other types of mills which are known to those skilled in the art and are suitable for wet milling, for example an upright or horizontal stirred ball mill. The solvent is preferably kept at room temperature by circulation in all sections. In addition, an internal cooling circuit can be provided in the mill in order to eliminate temperature gradients which may occur.

As an alternative, the suspension can also be activated by means of various dispersing apparatuses, e.g. by means of dissolvers or planetary dissolvers. Here, the metal oxide powder is dispersed in water by means of a dissolver disc and dispersed further at a circumferential velocity of at least 8 m/s, preferably at least 12 m/s, for at least 25 minutes. To set particle, aggregate and agglomerate size, the suspension is finely dispersed for at least 25 minutes by means of a dissolver, ultrasonic disperser, planetary dissolver, high-energy mill or highly clean ball mill.

As an alternative to preliminary suspension of the metal oxide in the liquid and subsequent activation of the suspension in two separate steps, the solid (metal oxide and/or mixture of various metal oxides) can also be added to the solvent during the activation step. Regardless of whether the solid is introduced beforehand or during the activation step, the treatment is preferably continued for a time of from 0.5 to 4 hours after addition of the solid is complete.

For the production of the activated metal oxide suspension by milling, it is possible to use milling media such as beads made of steel, glass, aluminium oxide, zirconium oxide, zirconium silicate, silicon carbide, silicon nitride or other materials known to those skilled in the art. Preference is given to materials composed of zirconium silicate, zirconium oxide, silicon nitride, particularly preferably silicon nitride. The milling bead diameters are usually from 0.8 to 2.0 millimeters.

A very homogeneous suspension should be produced in the production of the suspension. For the purposes of the invention, a homogeneous suspension is present when the suspension is virtually free of agglomerates. Agglomerates produce inhomogeneities in the future ceramic microstructure of the respective use, e.g. as catalyst support. To ensure freedom from agglomerates, the suspensions can also be freed of residual agglomerates by sieving at the end of the dispersion step.

A low viscosity (e.g. <2 Pa s) and flow limit are important for optimal homogenization of the suspension. These can be achieved by alteration of the pH. In the case of pyrogenic silicon dioxide, this can be effected by addition of an acid.

The pH is kept in a range from 2.0 to 4.0, preferably from 2.5 to 3.5, both during preliminary suspension and during the activation step. This can be effected by optional addition of an acid or a base. As acid or base, it is possible to use all mineral or nonmineral acids or bases known to those skilled in the art which later leave no impurities, or only negligible amounts of impurities, in the shaped body. Hydrochloric acid or nitric acid is preferably used as acid and ammonia, preferably an aqueous ammonia solution, is preferably used as base.

The solids content of the metal oxide suspension is preferably from 5 to 40% by weight, more preferably from 10 to 30% by weight and most preferably from 15 to 25% by weight. This is independent of whether the metal oxide suspension has been produced in two separate steps or the metal oxide powder has been added only during the activation step.

In the coagulation step, the suspension containing the activated metal oxide is converted by means of a pH change or by further addition of one or more metal oxides from its homogeneous, stable, fluid state into a state in which the suspension coagulates and thickens to produce a paste-like mass. The coagulated state can be regarded as a viscoelastic solid, i.e. the storage modulus G' is several times the loss modulus G".

The metal oxide added for coagulation can differ from the metal oxide added in the preliminary suspension and/or the activation step.

If the coagulation to form a paste-like mass is carried out by stirring further, pulverulent metal oxide or mixtures of various metal oxides into the suspension, this can, if appropriate, also be accompanied by additional addition of a base, for example aqueous ammonia solution, in order to aid the gelling process.

Up to the end of the addition of further pulverulent metal oxide, the pH can be kept in the range from 2 to 4 by optional addition of an acid, for example hydrochloric acid. After the addition of the additional amount of solid is complete, the pH can, if appropriate, be set in the range from 4 to 10, more preferably in the range from 5 to 8, by dropwise addition of a base, for example an aqueous ammonia solution, while stirring. Here, changing the pH and/or adding one or more metal oxides alters the rheology. A gel-like moulding composition is formed from a liquid suspension. The ratio of the amount of pulverulent metal oxide additionally added to the metal oxide present in the suspension is usually from 1:1 to 1 part of pulverulent metal oxide to 2 parts of metal oxide in suspension. While stirring in the metal oxide, care has to be taken to ensure that the metal oxide introduced is distributed very uniformly in the initial activated metal oxide suspension and inhomogeneities in the paste-like mass are avoided. Mixing of the metal oxide powder into the suspension using high shear forces should be avoided since otherwise the plasticity of the mass which is appropriate for the subsequent shaping step is lost again and the mass becomes too liquid. Leaving a suspension which is too liquid to stand for a longer time (a number of hours to days) can restore the appropriate plastic properties required for the later shaping steps.

As an alternative, the coagulation step can also be effected only by alteration of the pH. In this embodiment of the invention, no further metal oxide is added. Here, coagulation of the suspension is effected only by changing the pH by means of an acid or base. In the case of silicon dioxide, the pH is preferably adjusted with the aid of bases such as NaOH, KOH, NH3 or their aqueous solutions. These are added slowly, preferably dropwise, to the activated suspension to a final value in the range from 4 to 10, more preferably from 5 to 8. Particular preference is given to using NH3 here. The suspension can be converted by addition of NH3 from its homogeneous, stable, fluid range into a range in which the suspension coagulates and thickens.

It has surprisingly been found that the suspension was particularly suitable for shaping, preferably after little addition of NH3. A typical ratio of pyrogenic silicon dioxide, which on its own has a pH of from 3.9 to 4.5, to 1% NH3 solution is 45:1. Stable shaped bodies can be formed when the suspension is brought to a pH of from 5.6 to 6.9, preferably from 6.0 to 6.4. The pH of the resulting suspension is thus just below the neutral value of 7.0. After being brought to the above pH, the suspension coagulates within a few minutes to form a shapable mass having viscoelastic behaviour.

Viscoelastic behaviour means that in a rheological deformation experiment in oscillation, the storage modulus G' is greater than the loss modulus G". The moduli G' and G" can be determined according to the equation $\tau=\gamma(t)*(G' \sin \omega t + G'' \cos \omega t)$, where $\tau$ is the stress response of the specimen to the change in the deformation as a function of time $\gamma(t)$ at a maximum amplitude $\gamma_0$ and the angular velocity $\omega$, i.e. $\gamma(t)=\gamma_0*\sin \omega t$. The absolute values of G' and G" are determined in the plateau region of the storage modulus G'. The storage modulus G' should, for the purposes of the invention, be at least 10,000 Pa, preferably at least 50,000 Pa, and the ratio G"/G' should be less than 1, preferably less than 0.55 and most preferably less than 0.25. The respective modulus was measured by means of a plate-plate geometry having a shearing gap of 1.5 mm or in another embodiment of 2 mm at a temperature of 23° C.

The use according to the invention of the inventive mass displays particularly good long-term stability of the viscoelastic behaviour. This means that after a storage time of 1 week at room temperature in a closed container, the storage modulus G' has dropped at most to 70% of the initial value, preferably at most to 90% of the initial value, with the modulus being measured by means of a plate-plate geometry having a shearing gap of 1.5 mm or in another embodiment of 2.0 mm at a temperature of 23° C.

If mixing of the masses is insufficient, inhomogeneities within the moulding composition can influence the subsequent shaping step in an undesirable way. In this case, shaped bodies having a relatively low mechanical stability or masses which are absolutely unsuitable for shaping are formed. The proportion of solid metal oxide in the moulding composition is, for example in the case of support materials based on pyrogenic $SiO_2$, from 10 to 40% by weight.

If tableting is carried out later as shaping step, it is advantageous to choose a significantly higher solids content. If precipitated metal oxide particles are added to the pyrogenic metal oxide particles, it is possible, for example in the case of precipitated silica, to increase the solids content of the dispersion from 40% by weight to up to 60% by weight.

The shaping of the mass can be effected, for example, by extrusion, tableting or pressing. The shaped catalyst body is preferably produced by extrusion. Here, it is possible to conceive of all apparatuses known to those skilled in the art, e.g. extruders, screw extruders, tableting machines, continuous presses, ram extruders. Preference is given to using a ram extruder which when used for the moulding composition exerts no further shear forces, or only small shear forces, which could lead to liquefaction of the composition or phase separation of the moulding composition.

The geometry of the shaped catalyst body is determined by the shaping tool selected in each case. It is possible to produce geometries such as rings, pellets, cylinders, wagon wheels, spheres, etc. The length of rings and pellets is defined by use of a cutting device directly after shaping. The shaped body is dried by means of methods known to those skilled in the art (drying oven, IR heating, microwave). Drying is carried out at temperatures in the range from 25° C. to 200° C., preferably from 30° C. to 100° C., and more preferably from 40° C. to 80° C. The drying time depends on the ratio of metal oxide to water, but is in the range from 0.5 to 50 hours, preferably from 2 to 30 hours.

The drying of the shaped catalyst bodies is very critical since excessively fast drying (for example temperatures which are too high or atmospheric humidity which is too low) does not allow moisture which is still present to escape quickly enough from the material via the pores and thus leads to cracks being formed in the bodies.

After the shaped catalyst bodies have been dried, they are subjected to calcination. Possible calcination processes are all customary processes known to those skilled in the art.

Preference is given to calcination in the furnace under an air atmosphere, with the oxygen content being able to be varied. A further gas can be mixed into the air. Various protective gases are possible here. Suitable protective gases are all protective gases known to those skilled in the art, most preferably nitrogen, argon or helium. The air can likewise be replaced completely by the protective gas. The calcination is carried out at temperatures in the range from 500° C. to 1250° C., preferably from 700° C. to 1100° C. and most preferably from 850° C. to 1000° C. The sintering time is in the range from 0.5 to 20 hours; a typical sintering time is in the range from 2 to 10 hours. The calcination can be carried out under atmospheric pressure or under reduced pressure. The process of the invention enables equal strengths to be achieved at lower calcination temperatures than are customary in the prior art.

The calcination step reduces the surface area of the catalyst support, which is an important parameter for the catalytic process. However, since the support materials according to the invention demonstrate satisfactory stability even without calcination or after calcination at low temperatures because of their excellent homogeneity, they have not only the higher purity but also significantly higher support surface areas and pore volumes compared to the prior art.

Furthermore, the shaped catalyst bodies obtained from the process of the invention are produced without the customary addition of auxiliaries/additives, for example extrusion aids, pore formers or sols. Dispensing with auxiliaries enables the high chemical purity of the (for example pyrogenic) metal oxides to be retained. The support shape of the materials is not critical for the process of the invention. Whether the active components are added to the paste-like mass before the shaping step and are therefore already more or less finely distributed on the support material after the shaping step or are applied only after the final production of the catalyst support in a subsequent process step, e.g. by impregnation, is likewise not critical for the invention.

Owing to the high purity of the starting powders and the high-purity production process, targeted doping of the high-purity metal oxide with another high-purity metal oxide is possible. An example is the production of acidic catalyst supports by doping pyrogenic $SiO_2$ with pyrogenic $Al_2O_3$. This doping creates Lewis-acid sites in the $SiO_2$. High-purity mixed oxides can be produced according to this principle from the high-purity oxides $SiO_2$, $Al_2O_3$, $ZrO_2$ and $TiO_2$. Preferably, metal oxides of the formulae $Si_xO_y$, $Al_xO_y$, $Ti_xO_y$, $Zr_xO_y$, and $Ce_xO_y$ are used as the metal oxides, where x and y are such that the metal oxide $M_xO_y$ is neutral.

The high purity of the undoped shaped bodies produced also allows doping with other inorganic dopants. A condition is that the sum of impurities, i.e. all elements apart from the metal oxides $M_xO_y$ used or mixtures of various metal oxides, for example when using silicon dioxide Si and O, is always less than 400 ppm, preferably less than 100 ppm, and more preferably less than 20 ppm. Shaped bodies having a sum of impurities (all metals and also phosphorus and sulphur and carbon) of less than 10 ppm and in the ideal case even less than 1 ppm can be produced by the process of the invention.

As dopants, it is possible to select inorganic metal salts. These can be, for example, halides, oxides, nitrates, nitrites, silicates, carbonates, borates, aluminates, molybdates, tungstates, vanadates, niobates, tantalates, titanates or zirconates. It is in principle possible to use any cationic species as counterion to this anionic component. The counterion is preferably a cation from the group consisting of alkali metals or alkaline earth metal ions. Very particular preference is given to using an alkali metal cation.

The use of finely divided oxides results in formation of shaped catalyst bodies having very high surface areas. The BET surface areas achieved are in the range from 30 m²/g to 500 m²/g, preferably from 150 m²/g to 450 m²/g and most preferably from 250 m²/g to 400 m²/g. The finely divided oxides also result in production of a shaped body having a high pore volume in the range from 0.5 ml/g to 1.3 ml/g, preferably from 0.7 ml/g to 1.25 ml/g and more preferably from 0.9 ml/g to 1.2 ml/g.

Shaped bodies having fine pores can be formed from the finely divided metal oxides by means of sintering. The proportion of pores having a diameter in the range from 10 nm to 20 nm is typically more than 60%, preferably more than 70% and most preferably more than 80%.

The conversion of the shaped body into an active catalyst is achieved by application of one or more catalytically active compounds or one or more precursor compounds and/or one or more promoter compounds which can be converted into one or more catalytically active compounds in a subsequent step. Here, it is possible to use all processes known to those skilled in the art which lead to catalysts for the gas-phase oxidation of olefins. The use of the high-purity and high-surface-area support bodies according to the invention thus makes it possible to obtain previously unachievable high surface areas and a very fine distribution of the noble metal sites together with the associated higher catalyst activity.

The addition of one or more promoter compounds can also be carried out in a separate step after conversion of the shaped bodies into a catalyst.

As an alternative to application of one or more catalytically active compounds or one or more precursor compounds together with one or more promoter compounds in one step, the application of one or more promoter compounds can be carried out separately in a process step preceding or following the application of one or more catalytically active compounds or one or more precursor compounds.

The finished catalysts have advantages in respect of activity (space-time yield), selectivity (reduced secondary reaction: ethene combustion to carbon dioxide and lower ethyl acetate formation) and/or long-term stability as a result of the novel high-surface-area support materials on which they are based.

As catalytic components for coating the shaped bodies, preference is given to using one or more systems from the group consisting of Pd/Au/alkali metal compounds, Pd/Cd/alkali metal compounds and Pd/Ba/alkali metal compounds in the process of the invention.

Here, one or more of the abovementioned components are applied to the support by impregnation, spraying, vapour deposition, dipping or precipitation of the Pd and/or Au and/or Cd and/or Ba metal compounds. If appropriate, these components can also be applied by reduction of the reducible metal compounds applied to the support and/or washing to remove any chloride present, by impregnation with alkali metal acetate or alkali metal compounds which are converted completely or partly into alkali metal acetate under the reaction conditions in the production of vinyl acetate monomer, in an appropriate order.

As alkali metal compounds, preference is given to using potassium compounds such as potassium acetate. All further components and/or promoters for increasing the catalyst activity and/or catalyst selectivity which are known to those skilled in the art are likewise possible.

The coating step of the process of the invention is described in more detail below for the production of supported catalysts for the example of the system Pd/alkali metal/Au. Shaped bodies, in particular in the form of hollow cylinders (ring extrudates), are, according to one embodiment of the invention, impregnated with a solution containing palladium and/or gold. At the same time as the impregnation with the solution or solutions containing noble metals or in succession in any order, the support materials used can be impregnated with a basic solution which can contain one or more basic compounds. The basic compound or compounds serve(s) to convert the palladium compound and gold compound into their hydroxides.

The application of various noble metal compounds can be carried out in one step or in a plurality of successive steps. Between these steps, it is also possible to carry out intermediate drying and/or calcination and/or one or more reduction steps.

As an alternative to the addition of a base after application of the solution or solutions containing noble metal, the addition of base can also be carried out simultaneously with the solution or solutions containing noble metal.

In a further embodiment, the shaped body can firstly have one or more basic compounds applied to it before one or more solutions containing noble metal are added.

An intermediate drying step can be carried out between the application of one or more basic compounds and the application of the noble metals.

The compounds in the basic solution can consist of alkali metal hydroxides, alkali metal bicarbonates, alkali metal carbonates, alkali metal silicates or mixtures of these substances. Preference is given to using potassium hydroxide, sodium hydroxide and/or sodium metasilicate.

To prepare the solution containing noble metal, it is possible to use, for example, palladium chloride, sodium or potassium palladium chloride, palladium acetate or palladium nitrate as palladium salts. Suitable gold salts are gold (III) chloride and tetrachloroauric(III) acid. Preference is given to using potassium palladium chloride, sodium palladium chloride and/or tetrachloroauric acid.

The impregnation of the catalyst support with the basic solution influences the precipitation of the noble metals on the catalyst support. The basic solution can be brought into contact with this solution either before, simultaneously with the noble metal solution or after application of the noble metal salt or salts. In the case of successive impregnation of the catalyst support with the two solutions, intermediate drying and/or reduction and/or calcination can be carried out after the first impregnation step.

The thickness of the surface shell can be influenced by the amount of basic compound applied to the support material relative to the desired amount of the noble metals. The higher this ratio, the lower the thickness of the shell formed. The ratio of basic compound to noble metal compounds required for a desired shell thickness can depend on the nature of the support material and on the basic compound and noble metal compounds selected. The required ratio is advantageously determined by means of a few preliminary tests. The shell thickness obtained can be determined in a simple manner by cutting open the catalyst particles.

The minimum required amount of the basic compound or compounds can be derived from the stoichiometrically calculated amount of hydroxide ions which are required for converting the palladium and the gold into the hydroxides. As a guideline, the basic compound should be employed in a 1- to 10-fold stoichiometric excess for a shell thickness of up to 1.0 mm.

The noble metal salts and the basic compounds can also be applied to the catalyst supports by the method of pore volume impregnation. If intermediate drying is employed, the volumes of the two solutions are chosen so that they each correspond to from 90 to 100% of the uptake capacity of the catalyst support. If intermediate drying is omitted, the sum of the individual volumes of the two impregnation solutions have to correspond to the above conditions, with the ratio of the individual volumes being able to be from 1:9 to 9:1. Preference is given to employing a volume ratio of from 3:7 to 7:3, in particular 1:1. Preference is given to using water as solvent in both cases. However, it is also possible to use suitable organic or aqueous-organic solvents.

The reaction of the noble metal salt solution with the basic solution to form insoluble noble metal compounds can occur slowly and is, depending on the method of preparation, generally complete only after from 1 to 24 hours. The water-insoluble noble metal compounds are then treated with reducing agents. It is possible to carry out a wet reduction, for example using aqueous hydrazine hydrate or formaldehyde, or a gas-phase reduction using hydrogen, ethene or a hydrogen/nitrogen mixture, for example. The reduction can be carried out at room temperature or elevated temperature and at atmospheric pressure or superatmospheric pressure, if appropriate with addition of inert gases such as nitrogen.

Before and/or after reduction of the noble metal compounds, any chloride present on the support can be removed by thorough washing. The washing of the catalyst is carried out using water, particularly preferably a basic aqueous solution (pH>7), most preferably with a solution having a pH of 8-12. After washing, the catalyst preferably contains less than 500 ppm of chloride, more preferably less than 200 ppm of chloride.

The catalyst precursor obtained after reduction can be dried and finally impregnated with alkali metal acetates or alkali metal compounds which are converted completely or partly into alkali metal acetates under the reaction conditions in the production of vinyl acetate monomer. Impregnation with potassium acetate is preferred. Here, pore volume impregnation can again preferably be employed. This means that the required amount of potassium acetate is dissolved in a solvent, preferably water, whose volume corresponds approximately to the uptake capacity of the initially charged support material for the total solvent. This volume is approximately equal to the total pore volume of the support material.

The finished catalyst can subsequently be dried to a residual moisture content of less than 5%. Drying can be carried out in air, if appropriate under nitrogen as inert gas.

The coating step of the process of the invention is described in more detail below for the production of supported catalysts for the example of the systems Pd/alkali metal/Ba and Pd/alkali metal/Cd.

In the production of Pd/alkali metal/Ba and Pd/alkali metal/Cd catalysts, the metal salts can be applied by known methods such as impregnation, spraying, vapour deposition, dipping or precipitation. The detailed production of supported catalysts of the systems Pd/alkali metal/Cd and Pd/alkali metal/Ba on suitable support materials is described in U.S. Pat. No. 4,093,559 (Pd/Cd) and EP 565952 (Pd/Ba without ultrasonic atomization), which are hereby incorporated by reference.

For the synthesis of vinyl acetate monomer, it is advantageous to coat the catalyst with from 0.1 to 5.0% by weight of palladium and from 0.2 to 3.5% by weight of gold or from 0.1 to 3.5% by weight of cadmium or from 0.1 to 3.5% by weight of barium and from 0.5 to 15% by weight of potassium, in each case based on the weight of the support used. The loadings can vary depending on the catalyst system used (Pd/Au system, Pd/Cd system or Pd/Ba system). In the case of catalyst supports having a bulk density of, for example, 500 g/l, the concentration figures correspond to volume-based concentrations of from 0.5 to 25 g/l of palladium and from 1.0 to 17.5 g/l of gold or from 0.5 to 17.5 g/l of cadmium or from 0.5 to 17.5 g/l of barium and from 2.5 to 75 g/l of potassium.

The catalyst loadings are in detail:

The palladium content of the Pd/alkali metal/Au catalysts is from 0.2 to 3.5% by weight, preferably from 0.3 to 3.0% by weight.

The gold content of the Pd/alkali metal/Au catalysts is from 0.2 to 3.5% by weight, preferably from 0.3 to 3.0% by weight.

The potassium content of the Pd/alkali metal/Au catalyst is from 0.5 to 15% by weight, preferably from 1.0 to 12% by weight.

The palladium content of the Pd/alkali metal/Cd or Pd/alkali metal/Ba catalysts is from 0.1 to 5.0% by weight, preferably from 0.2 to 4.5% by weight.

The cadmium content of the Pd/alkali metal/Cd catalysts is from 0.1 to 3.5% by weight, preferably from 0.2 to 3.0% by weight.

The barium content of the Pd/alkali metal/Ba catalysts is from 0.1 to 3.5% by weight, preferably from 0.2 to 3.0% by weight.

The Ba content is preferably in the same range as the Cd content in Cd systems.

The potassium content of the Pd/alkali metal/Cd or Pd/alkali metal/Ba catalysts is from 0.3 to 10% by weight, preferably from 0.5 to 9% by weight.

To prepare the impregnation solutions, the appropriate amounts of the palladium and gold compounds can be dissolved in a volume of water which corresponds to from about 10 to about 100% of the water uptake capacity of the initially charged support material. The basic solution can be prepared in an analogous way.

The shaped bodies according to the invention display or make possible low pressure drops, low bulk densities, large external surface area per unit volume of a reaction vessel, good mass and heat transfer and, particularly compared to known hollow cylinders and other support shapes such as honeycomb-shaped support materials, significantly increased fracture strength and abrasion resistance.

The use of high-surface-area support materials in the catalysts of the invention enables, at a given amount of noble metal, the catalytically active noble metal sites to be separated from one another by a greater distance (increased long-term stability at the same activity) or higher noble metal loadings to be achieved at the same spacings (higher activity can be achieved at the same long-term stability). However, since a concentration of catalytically active metals (Pd/Au or the Pd/Cd or the Pd/Ba) which is too high leads to catalysts which reach excessively high temperature maxima with correspondingly greater formation of undesirable by-products, the catalyst composition has to be matched to the support material and balanced by the reactor geometry (heat removal).

The supported catalysts of the invention can be used for preparing unsaturated esters from olefins, organic acids and oxygen in the gas phase. In particular, the supported catalysts of the invention can be used for the production of vinyl acetate monomer. For this purpose, ethene, acetic acid and molecular oxygen or air are reacted in the gas phase, if appropriate with addition of inert gases, at temperatures of from 100 to 250° C. and at atmospheric or superatmospheric pressure, for example from 1 to 25 bar, in the presence of the supported catalyst of the invention. Space velocities based on the gas phase of from 1000 to 5000 standard liters of gas mixture per liter of catalyst and per hour are typically realized.

In the process for preparing vinyl acetate monomer, the reactants are initially passed over the catalyst at a low space velocity. During this running-up phase, the activity of the catalyst increases and usually reaches its final level only after days or weeks. The supported catalysts of the invention achieve a significantly improved product yield because of an increased activity and/or an improved selectivity.

The catalysts of the invention can also be used for the acetoxylation of olefins such as propene. The following examples illustrate the performance of the supported catalysts according to the invention based on hollow cylinders (ring extrudates). In particular, ring extrudates based on pyrogenic silicon dioxides are described in detail.

The bulk densities indicated are determined by filling a tube having an internal diameter of 33 millimeters.

Activity and selectivity of the catalysts from the following examples and comparative examples are measured over a period of up to 200 hours. The catalysts are tested in an oil-cooled flow reactor (reactor length=1200 mm, internal diameter=19 mm) at an absolute pressure of 9.5 bar and a space velocity (GHSV) of 3500 standard m$^3$/(m$^3$*h) using the following gas composition: 60% by volume of ethene, 19.5% by volume of carbon dioxide, 13% by volume of acetic acid and 7.5% by volume of oxygen. The catalysts are examined in the temperature range from 130 to 180° C., measured in the catalyst bed.

The reaction products are analyzed at the outlet of the reactor by means of on-line gas chromatography. The space-time yield of the catalyst in gram of vinyl acetate monomer per hour and liter of catalyst (g(VAM)/l$_{cat}$*h) is determined as a measure of the catalyst activity. Carbon dioxide, which is formed, in particular, by combustion of ethene, is likewise determined and used to assess the catalyst selectivity.

In addition to the determination of the reaction products in the gas phase, the liquid reaction products are collected in a vessel cooled to 15° C. and the condensate obtained is analyzed by means of gas chromatography to determine the liquid by-products (e.g. ethyl acetate). The amount of liquid by-products formed are always reported as a ratio to vinyl acetate monomer, e.g. ethyl acetate formation in mg(ethyl acetate)/g(VAM).

The BET surface area is determined in accordance with DIN 66131 using nitrogen.

The pore distribution is determined by means of mercury porosimetry. The determination of the pore volume is carried out in accordance with DIN 66134 (Langmuir, p/p$_0$=0.9995).

The strength is determined by means of a Zwick Z 010 materials testing machine fitted with a load cell having a nominal force of 1 kN, model II.

EXAMPLES

Example 1

Support Production by Means of Milling and Additional Metal Oxide 10 kilogram of pyrogenic silica (WACKER HDK® T40) are stirred into 40 kilogram of deionized water, circulated and milled for a period of 2 hours in a stirred ball mill using silicon nitride milling beads (diameter of the milling beads=2.0 mm, degree of fill=70% by volume). The angular velocity during the milling step is 11 meters per second. After completion of milling, 5 kilogram of pulverulent pyrogenic silica (WACKER HDK® T40) are stirred into the dispersion until a pasty, gel-like mass is formed. This mass is extruded on a ram extruder through a suitable tool to give the desired shapes and optionally cut to the desired length of the shaped body. The shaped bodies obtained, in this case rings having a length of 5.5 mm, an external diameter of 5.5 mm and a hole of 2.5 mm, are dried at a temperature of 85° C. and an atmospheric humidity of 75% for 24 hours and subsequently calcined at 900° C. for 8 hours. The support rings according to the invention have a surface area (BET surface area) of 290 m$^2$/g and a pore volume of 1.2 ml/g. The mechanical strength of the rings in the transverse direction is 10 N. The bulk density is 320 gram per liter.

Example 2

Support Production by Means of Milling and pH Adjustment 4 kilogram of pyrogenic silica (WACKER HDK® T40) are stirred into 35 kilogram of deionized water. A pH of 2.8 is set and kept constant by addition of hydrochloric acid. While stirring continually, a further 4.5 kilogram of pyrogenic silica (WACKER HDK® T40) are stirred in. After addition of the metal oxide powder is complete, the mixture is homogenized for a further 10 minutes before the suspension is milled in a stirred ball mill for 45 minutes using silicon nitride milling beads (diameter of the milling beads=2.0 mm, degree of fill=70% by volume) at a constant pH of 2.8 maintained by addition of further hydrochloric acid. The angular velocity during the milling step is 11 meters per second. After milling is complete, an aqueous ammonia solution is added to the suspension while stirring continually until a pH of 6.2 is obtained and gelling of the mass occurs at this point. The mass obtained is extruded on a ram extruder through a suitable tool to give the desired shapes and optionally cut to the desired length of the shaped body. The shaped bodies obtained, in this case rings having a length of 5.5 mm, an external diameter of 5.5 mm and a hole of 2.5 mm; are dried at a temperature of 85° C. and an atmospheric humidity of 70% for 24 hours and subsequently calcined at 900° C. for 2 hours. The support rings according to the invention have a surface area (BET surface area) of 260 m$^2$/g and a pore volume of 1.1 ml/g. The mechanical strength of the rings in the transverse direction is 10 N. The bulk density is 280 gram per liter.

Example 3

Support Production without Milling and with pH Adjustment 1155 g of twice-distilled H$_2$O are placed in a 4 liter plastic beaker. 345 g of pyrogenic silicon dioxide (WACKER HDK® T40) are stirred in using a plastic-coated dissolver at 1000 rpm. The mixture is subsequently stirred at 8000 rpm for another 30 minutes. The slip is transferred to a planetary mixer having 2 plastic-coated beam stirrers. At 100 rpm, 7.5 g of 1% strength (% by weight) aqueous ammonia solution are added dropwise. After the addition is complete, the mixture is stirred for another 10 minutes. The mixture is then introduced into a ram extruder. Rheology and pH of a sample are measured in parallel: G'=200,000, G"=25,000, pH=6.1.

The mass is extruded on a ram extruder through a suitable tool to give the desired shapes and cut to the desired length of the shaped body. The shaped bodies obtained, in this case rings having a length of 6 mm, an external diameter of 6 mm and a hole of 3 mm, are dried at a temperature of 85° C. and an atmospheric humidity of 70% for 24 hours. The support rings according to the invention have a surface area (BET surface area) of 350 m$^2$/g and a pore volume of 1.1 ml/g. The mechanical strength of the rings is 17 N. The bulk density is 340 gram per liter. The shaped bodies produced in this way contain the following impurities (all figures in ppm): Cu (0.03), Fe (2), Ti (0.05), Al (0.3), Ca (0.4), Mg (0.3), Na (0.3), K (0.2), Ni (0.5), Cr (0.03), P (0.06), C not detectable and S not detectable.

Example 4

500 gram of an SiO$_2$ support material from Example 1 are impregnated with 600 ml of an aqueous solution containing 27.60 gram of a 41.8% strength (% by weight) solution of tetrachloroauric acid and 42.20 gram of a 20.8% strength (% by weight) solution of tetrachloropalladic acid. After 2 hours, the catalyst is dried in a subsequent step at a temperature of 80° C. under reduced pressure for 5 hours. 236 ml of a 1 molar sodium carbonate solution together with 364 ml of distilled water are subsequently applied. After 2 hours, the catalyst is dried at a temperature of 80° C. under reduced pressure for 5 hours. The catalyst is subsequently washed with an aqueous ammonia solution having an ammonia content of 0.25% by weight for 45 hours. The catalyst is reduced by means of a hydrogen/nitrogen mixture (95% of $N_2$/5% of $H_2$) at a temperature of 200° C. for 5 hours. The catalyst is subsequently impregnated with an acetic acid-containing potassium acetate-solution (71.65 gram of potassium acetate in 600 ml of acetic acid) and finally dried at a temperature of 80° C. under reduced pressure for 5 hours. The finished catalyst has a concentration of 1.6% by weight of palladium (5.1 g/l), 2.1% by weight of gold (6.7 g/l) and 5.2% by weight of potassium (16.6 g/l).

When this catalyst according to the invention was tested in the reactor under the above-described conditions, activities of 800 g(VAM)/$l_{cat}$*h (156 g(VAM)/$g_{Pd}$*h) at ethene selectivities of 90.5% could be achieved. The ethyl acetate formation is 0.35 gram of ethyl acetate per kilogram of vinyl acetate formed.

Example 5

500 gram of an $SiO_2$ support material from Example 1 are prepared in a manner analogous to Example 4, but the concentrations of the impregnation solutions are selected so that the finished catalyst has a concentration of 2.0% by weight of palladium (6.4 g/l), 2.0% by weight of gold (6.4 g/l) and 6.5% by weight of potassium (20.8 g/l).

When this catalyst according to the invention was tested in the reactor under the above-described conditions, activities of 930 g(VAM)/$l_{cat}$*h (145 g(VAM)/$g_{Pd}$*h) at ethene selectivities of 92.5% could be achieved. The ethyl acetate formation is 0.35 gram of ethyl acetate per kilogram of vinyl acetate formed.

Example 6

80 gram of an $SiO_2$ support material from Example 2 are impregnated with 88 ml of an aqueous solution containing 4.43 gram of a 41.6% strength (% by weight) solution of tetrachloroauric acid and 7.03 gram of a 20.0% strength (% by weight) solution of tetrachloropalladic acid. After 2 hours, the catalyst is dried in a subsequent step at a temperature of 80° C. under reduced pressure for 5 hours. 37.8 ml of a 1 molar sodium carbonate solution together with 50 ml of distilled water are subsequently applied. After 2 hours, the catalyst is dried at a temperature of 80° C. under reduced pressure for 5 hours. The catalyst is subsequently washed with an aqueous ammonia solution having an ammonia content of 0.25% by weight for 30 hours. The catalyst is reduced by means of a hydrogen/nitrogen mixture (95% of $N_2$/5% of $H_2$) at a temperature of 200° C. for 5 hours. The catalyst is subsequently impregnated with an acetic acid-containing potassium acetate solution (11.46 gram of potassium acetate in 88 ml of acetic acid) and finally dried at a temperature of 80° C. under reduced pressure for 5 hours. The finished catalyst has a concentration of 1.6% by weight of palladium (4.5 g/l), 2.1% by weight of gold (5.9 g/l) and 5.2% by weight of potassium (14.6 g/l). When this catalyst according to the invention was tested in the reactor under the above-described conditions, activities of 750 g(VAM)/$l_{cat}$*h (167 g(VAM)/$g_{Pd}$*h) at ethene selectivities of 90.5% could be achieved. The ethyl acetate formation is 0.55 gram of ethyl acetate per kilogram of vinyl acetate formed.

Example 7

80 gram of an $SiO_2$ support material from Example 3 are impregnated with 88 ml of an aqueous solution containing 5.14 gram of a 41.6% strength (% by weight) solution of tetrachloroauric acid and 8.47 gram of a 20.0% strength (% by weight) solution of tetrachloropalladic acid. After 2 hours, the catalyst is dried in a subsequent step at a temperature of 80° C. under reduced pressure for 5 hours. 44.5 ml of a 1 molar sodium carbonate solution together with 43.5 ml of distilled water are subsequently applied. After 2 hours, the catalyst is dried at a temperature of 80° C. under reduced pressure for 5 hours. The catalyst is subsequently washed with an aqueous ammonia solution having an ammonia content of 0.25% by weight for 30 hours. The catalyst is reduced by means of a hydrogen/nitrogen mixture (95% of $N_2$/5% of $H_2$) at a temperature of 200° C. for 5 hours. The catalyst is subsequently impregnated with an acetic acid-containing potassium acetate solution (13.43 gram of potassium acetate in 88 ml of acetic acid) and finally dried at a temperature of 80° C. under reduced pressure for 5 hours. The finished catalyst has a concentration of 1.9% by weight of palladium (6.5 g/l), 2.4% by weight of gold (8.2 g/l) and 6.0% by weight of potassium (20.4 g/l). When this catalyst according to the invention was tested in the reactor under the above-described conditions, activities of 800 g(VAM)/$l_{cat}$*h (124 g(VAM)/$g_{Pd}$*h) at ethene selectivities of 90.2% could be achieved. The ethyl acetate formation is 0.45 gram of ethyl acetate per kilogram of vinyl acetate formed.

Comparative Example 1

60 gram of spherical support materials having a diameter of 6 millimeter based on bentonite (KA-120, from Sud Chemie; bulk density=540 gram/liter) are impregnated with 36 ml of an aqueous solution containing 0.80 gram of gold chloride and 2.0 gram of palladium acetate. After 2 hours, the catalyst is dried in a subsequent step at a temperature of 80° C. under reduced pressure for 4 hours. 28.2 ml of a 1 molar potassium carbonate solution together with 8 ml of distilled water are subsequently applied. After 2 hours, the catalyst is dried at a temperature of 80° C. under reduced pressure for 5 hours. The catalyst is subsequently washed with an aqueous ammonia solution having an ammonia content of 0.25% by weight for 60 hours. The catalyst is reduced by means of a hydrogen/nitrogen mixture (95% of $N_2$/5% of $H_2$) at a temperature of 200° C. for 5 hours. The catalyst is subsequently impregnated with an acetic acid-containing potassium acetate solution (3.30 gram of potassium acetate in 36 ml of acetic acid) and finally dried at a temperature of 80° C. under reduced pressure for 4 hours. The finished catalyst has a concentration of 1.5% by weight of palladium (8.1 g/l), 0.7% by weight of gold (3.8 g/l) and 2.1% by weight of potassium (11.3 g/l). When this catalyst according to the invention was tested in the reactor under the above-described conditions, activities of 680 g(VAM)/$l_{cat}$*h (84 g(VAM)/$g_{Pd}$*h) at ethene selectivities of 89.0% could be achieved. The ethyl acetate formation is 1.90 gram of ethyl acetate per kilogram of vinyl acetate formed.

Example 8

Pd/Cd System 100 gram of an $SiO_2$ support material from Example 1 are impregnated with 120 ml of an acetic acid-containing solution containing 5.17 gram of cadmium acetate, 6.02 gram of potassium acetate, 8.74 gram of palladium acetate and 1.33 gram manganese acetate. After 2 hours, the catalyst is dried at a temperature of 80° C. under reduced pressure for 5 hours. The finished catalyst has a concentration of 3.8% by weight of palladium (12.2 g/l), 2.0% by weight of cadmium (6.4 g/l), 2.2% by weight of potassium (7.0 g/l) and 0.25% by weight of manganese (0.8 g/l).

When this catalyst according to the invention was tested in the reactor under the above-described conditions, activities of 900 g(VAM)/l$_{cat}$*h (74 g(VAM)/g$_{Pd}$*h) at ethene selectivities of 92.8% could be achieved. The ethyl acetate formation is 0.70 gram of ethyl acetate per kilogram of vinyl acetate formed.

Comparative Example 2

Pd/Cd System 100 gram of spherical support materials having a diameter of 6 millimeter based on bentonite (KA-120, from Suid Chemie; bulk density 540 gram/liter) are impregnated with 60 ml of an acetic acid-containing solution containing 4.55 gram of cadmium acetate, 5.34 gram of potassium acetate, 5.17 gram of palladium acetate and 0.36 gram of manganese acetate. After 2 hours, the catalyst is dried at a temperature of 80° C. under reduced pressure for 5 hours. The finished catalyst has a concentration of 2.3% by weight of palladium (12.4 g/l), 1.8% by weight of cadmium (9.7 g/l), 2.0% by weight of potassium (10.8 g/l) and 0.07% by weight of manganese (0.4 g/l).

When this catalyst according to the invention was tested in the reactor under the above-described conditions, activities of 560 g(VAM)/l$_{cat}$*h (45 g(VAM)/g$_{Pd}$*h) at ethene selectivities of 92.8% could be achieved. The ethyl acetate formation is 1.30 gram of ethyl acetate per kilogram of vinyl acetate formed.

Example 9

Support Production without Milling and with pH Adjustment and with Addition of a Dopant 1155 g of twice-distilled H$_2$O are placed in a 4 liter plastic beaker. 345 g of pyrogenic silicon dioxide (Wacker HDK® T40) are stirred in using a plastic-coated dissolver at 1000 rpm. The mixture is subsequently stirred at a circumferential velocity of 14 m/s for 40 minutes. The slip is transferred to a planetary mixer having 2 plastic-coated beam stirrers. At 100 rpm, 8.5 g of 1% strength NH$_3$ solution are added dropwise. The pH of the resulting mass is 6.4.-45 mg of Na$_2$SiO$_3$ are then added. After the addition is complete, the mixture is stirred for another 5 minutes. The mixture is then introduced into a ram extruder. The rheology of a sample is measured in parallel: G'=320,000, G"=35,000.

The mass is extruded on a ram extruder through a suitable tool to give the desired shapes and cut to the desired length of the shaped body. The shaped bodies obtained, in this case rings having a length of 6 mm and a diameter of 6 mm, are dried at a temperature of 85° C. for 24 hours. The shaped body is subsequently sintered at 850° C. The shaped bodies according to the invention have a surface area (BET surface area) of 205 m$^2$/g and a pore volume of 0.75 ml/g. The mechanical strength of the rings is 45 N. The bulk density is 370 gram per liter. The shaped bodies produced in this way contain the following impurities (all figures in ppm): Cu (0.03), Fe (4), Ti (0.05), Al (1.1), Ca (1.2), Mg (0.3), Na (49), K (4), Ni (0.5), Cr (0.3), P (0.06), C not detectable and S not detectable.

Example 10

500 gram of an SiO$_2$ support material from Example 9 are impregnated with 375 ml of an aqueous solution containing 27.60 gram of a 41.8% strength (% by weight) solution of tetrachloroauric acid and 42.20 gram of a 20.8% strength (% by weight) solution of tetrachloropalladic acid. After 2 hours, the catalyst is dried in a subsequent step at a temperature of 80° C. under reduced pressure for 5 hours. 236 ml of a 1 molar sodium carbonate solution together with 139 ml of distilled water are subsequently applied. After 2 hours, the catalyst is dried at a temperature of 80° C. under reduced pressure for 5 hours. The catalyst is subsequently washed with an aqueous ammonia solution having an ammonia content of 0.25% by weight for 45 hours. The catalyst is reduced by means of a hydrogen/nitrogen mixture (95% of N$_2$/5% of H$_2$) at a temperature of 200° C. for 5 hours. The catalyst is subsequently impregnated with an acetic acid-containing potassium acetate solution (71.65 gram of potassium acetate in 375 ml of acetic acid) and finally dried at a temperature of 80° C. under reduced pressure for 5 hours. The finished catalyst has a concentration of 2.0% by weight of palladium (7.4 g/l), 2.0% by weight of gold (7.4 g/l) and 6.5% by weight of potassium (24.1 g/l). When this catalyst according to the invention was tested in the reactor under the above-described conditions, activities of 870 g(VAM)/l$_{cat}$*h (118 g(VAM)/g$_{Pd}$*h) at ethene selectivities of 92.4% could be achieved. The ethyl acetate formation is 0.35 gram of ethyl acetate per kilogram of vinyl acetate formed.

TABLE 1

| | Example 4 | Example 5 | Example 6 | Example 7 | Comparative Example 1 | Example 8 | Comparative Example 2 | Example 10 |
|---|---|---|---|---|---|---|---|---|
| Component | | | | | | | | |
| Pd [% by weight] | 1.6 | 2.0 | 1.6 | 1.9 | 1.5 | 3.8 | 2.3 | 2.0 |
| Au [% by weight] | 2.1 | 2.0 | 2.1 | 2.4 | 0.7 | 0 | 0 | 2.0 |
| Cd [% by weight] | 0 | 0 | 0 | 0 | 0 | 2.0 | 1.8 | 0 |
| K [% by weight] | 5.2 | 6.5 | 5.2 | 6.0 | 2.1 | 2.2 | 2.0 | 6.5 |
| Mn [% by weight] | 0 | 0 | 0 | 0 | 0 | 0.25 | 0.07 | 0 |
| STY | | | | | | | | |
| g(VAM)/l(cat)*h | 800 | 930 | 750 | 800 | 680 | 900 | 560 | 870 |
| g(VAM)/g(Pd)*h | 156 | 145 | 167 | 124 | 84 | 74 | 45 | 118 |
| Selectivities | | | | | | | | |
| Ethene [%] | 90.5 | 92.5 | 90.5 | 90.2 | 89.0 | 92.8 | 92.8 | 92.4 |
| Ethyl acetate [‰] based on VAM | 0.35 | 0.35 | 0.55 | 0.45 | 1.90 | 0.70 | 1.30 | 0.35 |

The invention claimed is:

1. A process for producing catalysts for the gas-phase oxidation of olefins, which comprises the steps:
   (1) suspending at least one pyrogenic metal oxide in a liquid phase to form a suspension,
   (2) converting the metal oxide into an active state in a continuous phase by producing a fine metal oxide dispersion by means of a dispersing apparatus and/or wet milling,
   (3) coagulating the dispersion to obtain a viscoelastic mass,
   (4) shaping the viscoelastic mass into a shaped body,
   (5) drying the shaped body,
   (6) calcining the shaped body obtained in step (5), to form a calcined shaped body,
   (7) converting the calcined shaped body into an active catalyst by applying one or more catalytically active compounds or catalyst precursor compounds which can be converted in a subsequent step into one or more catalytically active compounds, and optionally applying one or more promoter compounds.

2. The process of claim 1, wherein the at least one pyrogenic metal oxide is selected from the group consisting of oxides of silicon, aluminum, titanium, zirconium, and cerium.

3. The process of claim 2, wherein the at least one pyrogenic metal oxide is $SiO_2$.

4. The process of claim 1, wherein the continuous phase comprises water.

5. The process of claim 1, wherein the step of converting the pyrogenic metal oxide into an active state is carried out in a frictional mill, an annular gap mill or a stirred ball mill.

6. The process of claim 1, wherein the step of converting the pyrogenic metal oxide into an active state is carried out by means of one or more dispersing apparatuses selected from the group consisting of dissolvers, ultrasonic dispersers and planetary dissolvers.

7. The process of claim 1, wherein suspending of the at least one pyrogenic metal oxide in a liquid phase is carried out during the step of converting the pyrogenic metal oxide into an active state.

8. The process of claim 1, wherein the suspension is activated for a period of from 0.5 to 4 hours.

9. The process of claim 1, wherein one or more beads made of steel, glass, aluminum oxide, zirconium oxide, zirconium silicate, silicon carbide, or silicon nitride, are used as milling media in a stirred ball mill.

10. The process of claim 1, wherein the pH during suspending the at least one pyrogenic metal oxide and during the step of converting the at least one pyrogenic metal oxide into an active state is in the range of from 2.0 to 4.0.

11. The process of claim 10, wherein the pH is regulated by means of hydrochloric acid, nitric acid, ammonia, or an aqueous solution thereof.

12. The process of claim 1, wherein the solids content of the activated pyrogenic metal oxide dispersion is from 5 to 40% by weight.

13. The process of claim 1, wherein coagulation of the pyrogenic metal oxide dispersion is achieved by adjusting the pH, further addition of one or more metal oxides, or a combination thereof.

14. The process of claim 1, wherein coagulation of the pyrogenic metal oxide dispersion containing the activated pyrogenic metal oxide is achieved by adjusting the pH to a value in the range from 4 to 10.

15. The process of claim 1, wherein coagulation of the pyrogenic metal oxide dispersion containing the activated pyrogenic metal oxide is carried out by further addition of one or more metal oxides.

16. The process of claim 1, wherein shaping is carried out by extrusion, tableting, or pressing.

17. The process of claim 1, wherein the shaped bodies have the shape of rings, pellets, cylinders, wagon wheels or spheres.

18. The process of claim 1, wherein the shaped bodies are dried at temperatures in the range from 25° C. to 200° C.

19. The process of claim 1, wherein calcining is carried out under an air atmosphere, with the oxygen content optionally varied, and a further gas optionally being added to the air.

20. The process of claim 1, wherein calcining is carried out at a temperature in the range from 500° C. to 1250° C.

21. The process of claim 1, wherein the shaped catalyst bodies formed have a BET surface area in the range from 30 $m^2/g$ to 500 $m^2/g$.

22. The process of claim 1, wherein the addition of one or more promoter compounds is carried out in a separate step after at least partial conversion of the shaped bodies into a catalyst by addition of the catalytically active compounds or catalyst precursor compounds.

23. The process of claim 1, wherein application of one or more promoter compounds is carried out separately in a process step preceding or following the application of one or more catalytically active compounds or catalyst precursor compounds.

24. The process of claim 1, wherein the shaped bodies are coated with one or more catalytic systems selected from the group consisting of Pd/Au/alkali metal compounds, Pd/Cd/alkali metal compounds and Pd/Ba/alkali metal compounds.

25. The process of claim 24, wherein components of the one or more catalytic systems are applied in step (7) by means of impregnation, spraying, vapour deposition, dipping, precipitation of Pd and/or Au and/or Cd and/or Ba metal compounds on the shaped bodies, reduction of reducible metal compounds applied to the shaped bodies, washing to remove any chloride present, and impregnation with alkali metal acetate or alkali metal compounds, in an appropriate order.

26. The process of claim 25, wherein potassium compounds are used as alkali metal compounds.

27. The process of claim 1, wherein one or more noble metal compounds are applied as one or more catalytically active compounds or catalyst precursor compounds in one step or in a plurality of successive steps to a shaped body obtained in one or more of steps (4), (5), or (6), and one or more steps selected from the group consisting of intermediate drying, calcination, and reduction are optionally carried out between these successive steps.

28. The process of claim 1, wherein noble metal compounds as one or more catalytically active compounds or catalyst precursor compounds are added to the shaped body in step (7), and chloride present on the shaped body is removed by thorough washing before and/or after reduction of noble metal compounds.

29. The process of claim 28, wherein washing of the catalyst is carried out by means of water or a basic aqueous solution having a pH of >7.

30. The process of claim 1, wherein the catalyst comprises, based on the weight of the shaped body used, one or more components from the group consisting of from 0.1 to 5.0% by weight of palladium, from 0.2 to 3.5% by weight of gold, from 0.1 to 3.5% by weight of cadmium, from 0.1 to 3.5% by weight of barium and from 0.5 to 15% by weight of potassium.

31. The process of claim 1, wherein a noble metal as a catalytically active compound is applied to the shaped body in step (7), and the concentration of the noble metal is constant within the support body.

32. The process of claim 1, wherein a noble metal as a catalytically active compound is applied to the shaped body in step (7), and the concentration of the noble metal decreases from an accessible outer surface in the direction of an interior of the shaped body.

33. The process of claim 1, wherein the sum of all impurities in the catalyst is less than 400 ppm.

34. The process of claim 1, wherein the shaped body has a sum of impurities of all other metals other than the metal of the pyrogenic metal oxide, carbon, phosphorus, and sulphur, of less than 400 ppm.

35. The process of claim 1, further comprising a step of oxidizing olefins and/or organic acids by contacting the olefin and/or organic acids with a catalyst obtained by the process of claim 1.

36. The process of claim 35, wherein said oxidizing step provides for the production of vinyl acetate monomer.

37. The process of claim 35, wherein said oxidizing step provides for the acetoxylation of olefins.

* * * * *